United States Patent [19]

Tullos et al.

[11] Patent Number: 5,658,338
[45] Date of Patent: Aug. 19, 1997

[54] PROSTHETIC MODULAR BONE FIXATION MANTLE AND IMPLANT SYSTEM

[76] Inventors: Hugh S. Tullos, 2151 Troon Rd., Houston, Tex. 77019; Philip C. Noble, 2147 Swift Blvd., Houston, Tex. 77030

[21] Appl. No.: 536,975

[22] Filed: Sep. 29, 1995

[51] Int. Cl.[6] .................................................. A61F 2/28
[52] U.S. Cl. .................................................. 623/18; 623/22
[58] Field of Search ........................................ 623/16–23

[56] References Cited

U.S. PATENT DOCUMENTS

| | | | |
|---|---|---|---|
| 4,283,799 | 8/1981 | Pratt, Jr. et al. | 623/23 |
| 4,336,618 | 6/1982 | Raab. | |
| 4,417,571 | 11/1983 | Nelson et al. | 623/16 |
| 4,491,987 | 1/1985 | Park. | |
| 4,728,335 | 3/1988 | Jurgutis | 623/23 |
| 4,881,536 | 11/1989 | Noble et al. | 623/22 |
| 4,955,325 | 9/1990 | Zarnowski et al. | 623/22 |
| 5,080,680 | 1/1992 | Mikhail et al. | 623/23 |
| 5,314,493 | 5/1994 | Mikhail | 623/23 |
| 5,443,523 | 8/1995 | Mikhail | 623/23 |
| 5,507,814 | 4/1996 | Gilbert et al. | 623/22 |

OTHER PUBLICATIONS

In Vivo Evaluation of Recombinant Human Osteogenic Protein (rhOP–1) As a Bone Graft Substitute for Spine Fusions, Cook, et al. 8th Annual Meeting, Nass, Oct. 14–16, 1993 San Diego, CA.

Baylink, D.J., et al., "Growth Factors to Stimulate Bone Formation," *J. Bone and Mineral Rresearch*, vol. 8, Supp. 2, pp. S565–S572 (1993).

*Primary Examiner*—Randy C. Shay
*Attorney, Agent, or Firm*—Laura G. Barrow

[57] ABSTRACT

Prosthetic systems, specifically acetabular implant systems, each comprising a preformed modular mantle designed to secure an acetabular implant within the acetabulum are disclosed.

39 Claims, 12 Drawing Sheets

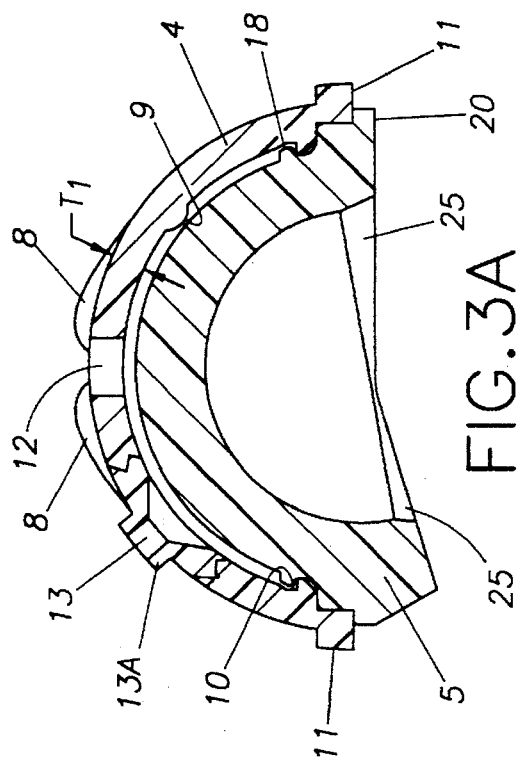
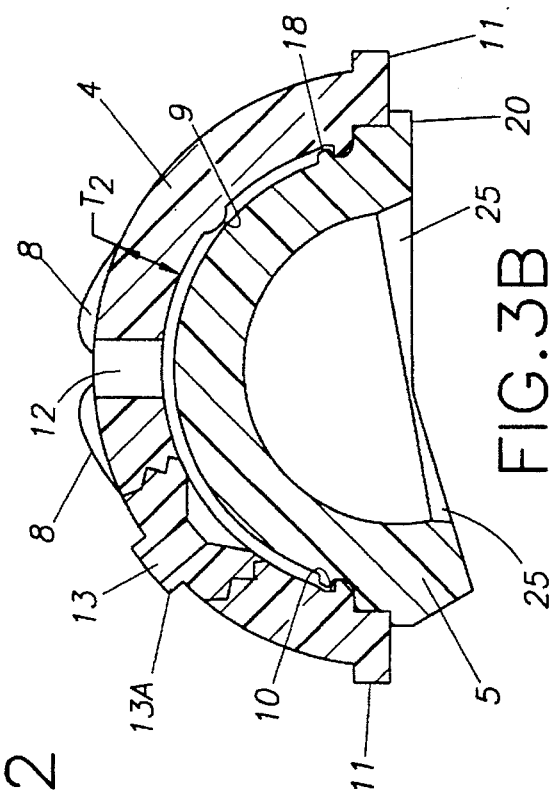
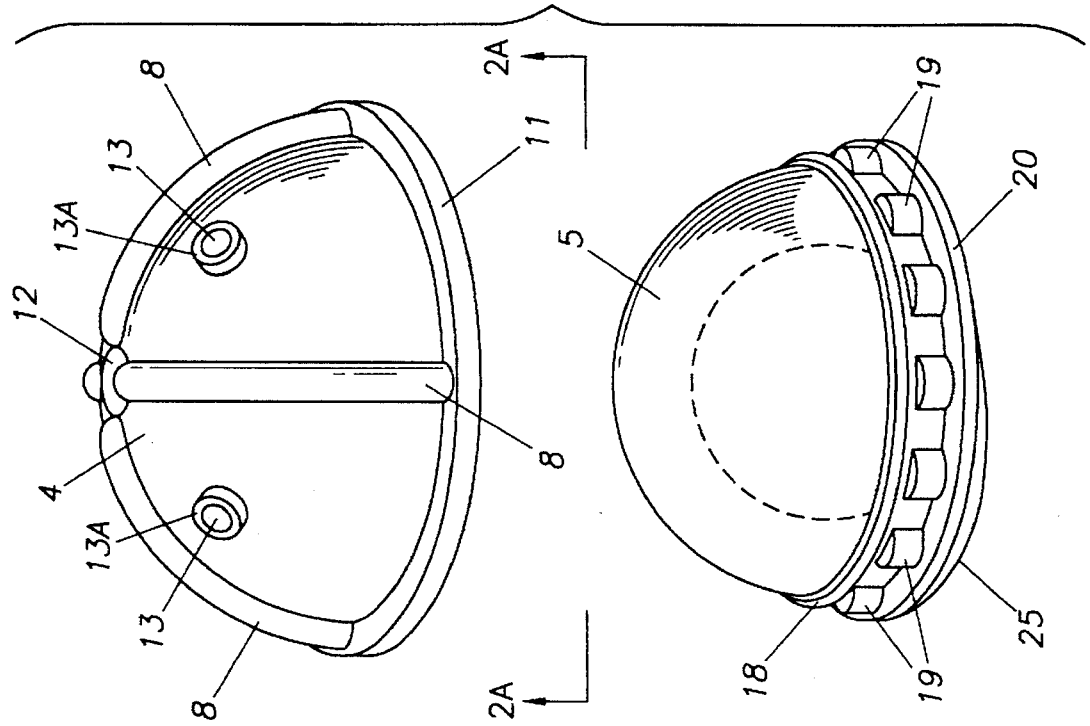

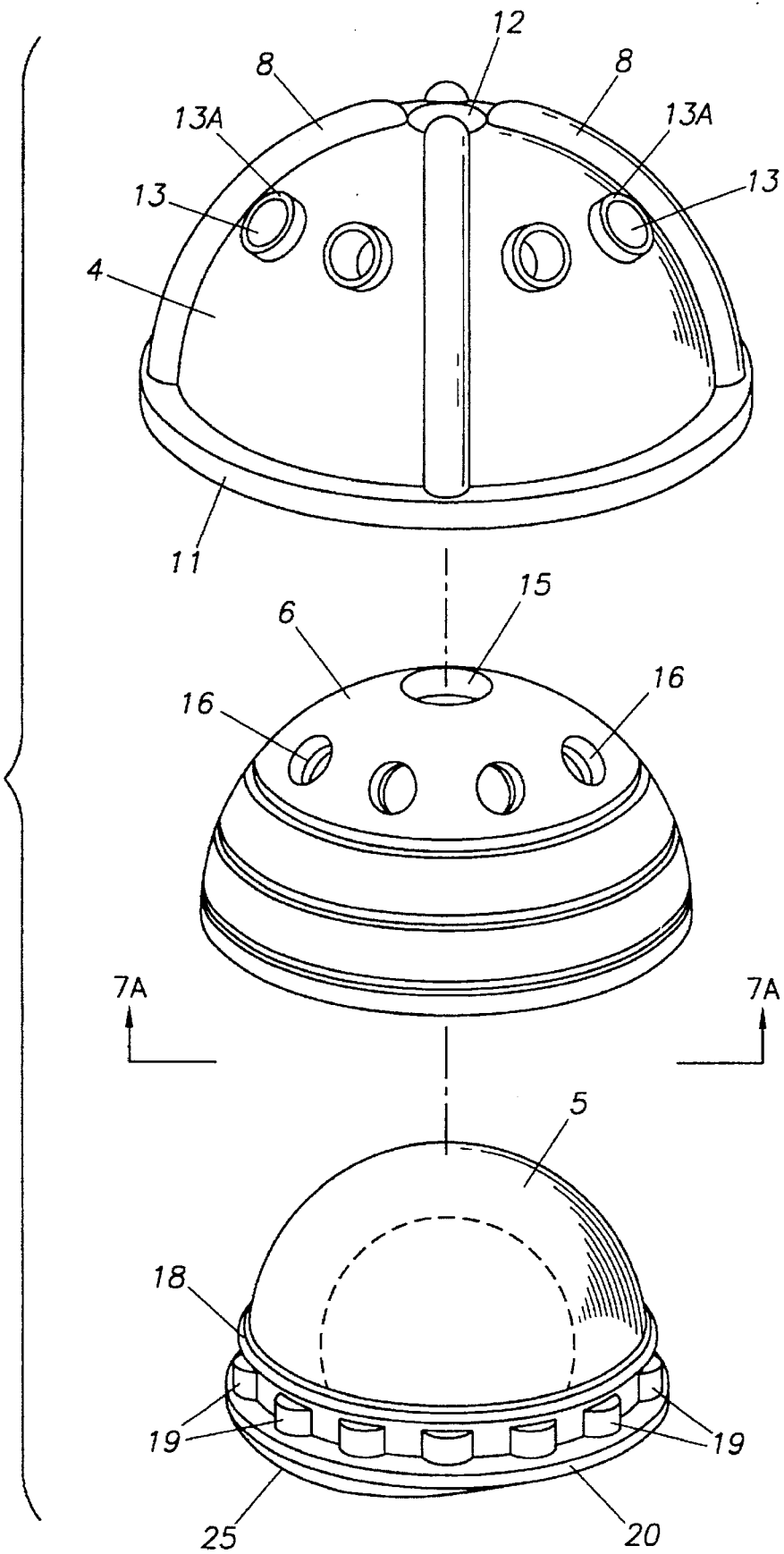

PROSTHETIC MODULAR BONE FIXATION MANTLE AND IMPLANT SYSTEM

BACKGROUND OF INVENTION

1. Field of Invention

The present invention relates to prosthetic implant systems, specifically replacement of the articulating surface of the pelvis (the acetabulum). The present invention relates to the use of modular preformed bone fixation mantles used to increase the versatility of existing acetabular replacements and to increase the durability of bone fixation of prosthetic acetabular cups to the skeleton.

2. Description of the Related Art

Total hip replacement is performed by replacing the worn surfaces of the hip joint with mechanical components fabricated from metal and plastic. The socket component (i.e. the acetabular cup) consists of a hemispherical shell, commonly manufactured from ultra high molecular weight polyethylene (UHMWPE) which can be directly fixed within the acetabulum of the pelvis with acrylic cement. Alternatively, the polymeric cup may be mechanically fixed to the reamed acetabulum by means of an intermediate metal shell to which the cup is fixed in surgery. This form of fixation is referred to as the "cementless mode". To render it stable within the pelvis under the action of joint loading, the metal shell generally has a porous outer surface into which bone and soft tissue can grow. At surgery, the shell is initially fixed to the bone, and the liner is then fixed in place within the shell. Typically, mechanical features within the inner surface of the shell and on the outer surface of the liner allow the surgeon to fix the liner in a desired rotational position within the shell. This allows the surgeon to maximize the mechanical stability of the prosthetic joint once the socket and the prosthetic femoral component are mated to form the artificial joint.

Cemented, single piece acetabular prostheses are fixed in place with acrylic cement which is introduced in a doughy or liquid form. Once the cement polymerizes, the outer surface of the shell becomes rigidly attached to the reamed surface of the acetabulum. Typically, the cement is delivered to the implantation site by hand or via a syringe. Once the acetabulum is filled with cement, the prosthetic component is pressed into the bed of cement until the surgeon determines that a satisfactory position has been obtained. At this point, excess cement which has extruded from the space between the bony socket and the prosthesis is removed and the prosthesis is held in position until the acrylic cement polymerizes. This may take from five to ten minutes.

Cement fixation has two major disadvantages. First, the strength of attachment of the cement to the bone depends upon the ability of the cement to penetrate the narrow, bloody interstices of the reamed bony bed of cancellous bone. To achieve this end, the cement must be forced into the bone under pressure. The cement, however, is difficult to pressurize with existing devices used for cement pressurization, thus many surgeons use the act of implantation to effect pressurization. Unfortunately, even this latter method is unsatisfactory because the cement pressure only becomes large enough to cause penetration of cement into the porous bone over the last few millimeters of implantation (i.e. when the peripheral gap has closed to less than about 1 mm). Cement mantles of this thickness (i.e. about 1 mm) are prone to fragment under repetitive weight-bearing, leading, ultimately, to loosening of the prosthesis. A second disadvantage is that during the process of driving the prosthesis into the acetabulum, the surgeon is not able to control its precise position with respect to the bony socket. Consequently, the polymeric surface of the prosthesis often contacts the bone in discrete areas, leaving areas with little or no cement mantle which can, once again, lead to fragmentation and loosening. Further, as soon as any part of the prosthesis contacts the walls or rim of the socket, the pressurizing force passes directly to the bone and pressurization is lost.

Previous attempts to solve the foregoing problems have included a variety of methods to pressurize cement within the acetabulum. Commonly proposed methods include the use of hemispherical compaction devices prior to implantation of the prosthesis. Others have developed special deformable or inflatable seals that are placed around the nozzle of the cement syringe and are forced into the implantation site. These devices attempt to fit the mouth of the acetabulum to allow the liquid cement to be injected under pressure without leakage. In general, these methods are unpopular and are relatively difficult to use effectively.

Previous attempts to improve fixation of joint prostheses to the cement include the use of femoral prostheses coated with a thin layer of polymerized cement, such as polymethylmethacrylate (PMMA). When the implant is inserted into the femur, the bone cement reacts chemically with the coating to provide a stronger adhesive bond between the implant and the cement mantle. These systems, such as those described in U.S. Pat. No. 4,336,618 to Raab and U.S. Pat. No. 4,491,987 to Park, for example, require relatively long, and sometimes complicated, procedures for preparing the cement-coated implant. While precoating is performed to increase the strength of the adhesive bond formed between the implant and the cement mantle, it is believed that it has no effect upon the strength of the cement itself or the bond formed between the cement mantle and bone. Moreover, it plays no role in controlling the alignment of the prosthesis or in controlling the thickness of the cement layer.

The cementless method of fixation of acetabular prostheses eliminates the use of acrylic cement and relies upon purely mechanical attachment of the prosthesis to the pelvis. Most "cementless" acetabular components consist of a metal shell and a polymeric liner. Typically, the metal shell is fixed to the acetabulum without cement, using instead an interference fit, metal screws, or both. Most shells have a rough porous outer (convex) surface which facilitates the development of friction between the shell and the bone during implantation. Typically, a shell is selected which is slightly larger (i.e. 1–3 mm) than the diameter of the reamed acetabulum. The shell is manually implanted into the bone. During this process, the surgeon attempts to control the position of the shell, particularly its angular orientation with respect to the bone and its depth of implantation. Once the shell is implanted, the surgeon may supplement its fixation by passing one or more screws through holes within the shell, thereby compressing the shell into the bone and increasing the stability of the interface between the shell and the socket.

The acetabular prosthesis is assembled by placing the polymeric liner into the hemispherical shell and locking it in place by impaction. Prior to assembly of the prosthesis, the preferred orientation of the liner within the shell is ascertained using a facsimile of the liner which does not engage the locking features of the shell. During this procedure, the femoral prosthesis is mated with the facsimile, and the artificial joint is moved to its extremes of motion to determine whether it will provide adequate excursion without dislocation or instability. In the event that insufficient motion is present, the surgeon is able to rotate the liner within the shell or replace the liner with another of a different design in order to increase the amount of stable motion. The ability of the surgeon to revise the position of the liner within the shell is one of the advantages of the two-piece modular construct. Once the surgeon has selected the best combination of design and orientation of the liner, the acetabular prosthesis is impacted, and the implantation is complete.

Cementless acetabular prostheses have a number of disadvantages, however. The initial stability of attachment of the prosthesis to the pelvis is not as rigid as those provided by fixation with acrylic cement. This can lead to pain and even dislodgement of the shell from the acetabulum. With time, tissue grows into the surface of the metal shell, but only a small proportion of the available surface is directly bonded to bone, leaving the rest of the interface susceptible to infiltration by small particles generated through wear of the polymeric articulating surface. Though cemented cups also have disadvantages, the bone cement at least provides an effective method of sealing off the interface with the underlying bone, thereby slowing or limiting the intrusion of wear particles.

Cementless acetabular prostheses also increase the cost of the joint replacement procedure. This is primarily due to two factors that contribute to much of the cost of manufacture: (i) the metal shell generally has a porous outer surface to promote ingrowth of bone, and (ii) the inner (concave) surface of the shell must be precisely machined and toleranced to ensure that the polymeric liner locks into place with minimal relative motion between the liner and the shell during subsequent loading within the body.

U.S. Pat. No. 4,955,325 to Zarnowski, et al. describes a method of converting a cementless acetabular cup component to one suitable for cemented affixation by means of attaching a plurality of spacers to the outside surface of the cup. While this theoretically allows a uniform layer of bone cement to form between the shell and the acetabulum and may reduce the incidence of direct impingement of the prosthesis on the underlying bone, the cement layer is not applied under pressure, and thus many of the same problems associated with cemented prostheses are still present. Moreover, the spacers are discontinuous and do not seal the implantation site during implantation of the prosthesis. Consequently, the spacers do not enhance the pressurization of the liquid cement to any significant degree.

It is therefore desireable to have a prosthetic system that combines the benefits of cemented and cementless acetabular prostheses. In particular, it is desireable to have a prosthetic system that has many of the following attributes:

(1) controls the thickness of the mantle;

(2) prevents direct impingement of the prosthesis on the underlying bone;

(3) allows the bone cement, when used, to be pressurized during implantation of the prosthetic acetabular shell without compromising the thickness of the mantle;

(4) allows the rotational position of the polymeric articulating surface to be altered after testing the range of motion of the joint without risk of damage to the acetabulum;

(5) allows a metal prosthetic acetabular shell designed primarily for use without cement to be utilized with cement or bone fixation enhancing substance without any modification prior to surgery; and (6) is cost effective by minimizing the need for a large number of different sizes of costly metal and/or polymeric prostheses.

SUMMARY OF THE INVENTION

The present invention is directed in part to a prosthetic system for implantation into a mammalian bone socket, in particular a hip implant system, comprising a modular preformed mantle designed for attaching a metal or polymeric prosthetic acetabular component to the acetabulum. The inventive modular mantle is designed to mate and be affixed to the surface of the acetabulum and the outer surface of the acetabular implant.

Specifically, the invention, in certain aspects, is a modular prosthetic system for implantation into a mammalian bone socket, wherein the system includes (1) a first prosthetic implant having an outer surface and an inner surface and (2) a modular mantle formed of a polymeric material having an outer surface and an inner surface, wherein the inner surface of the modular mantle is configured to complement the outer surface of the first implant and the outer surface of the modular mantle is configured to complement the bone socket. The invention also includes, in certain aspects, a second prosthetic implant having an outer surface configured to complement the inner surface of the first implant and a means for securing the second prosthetic implant to the first implant.

In one embodiment, the modular preformed mantle is formed of a polymeric cement and includes at least one port, preferably positioned toward the apex of the modular mantle, through which liquid bone cement may be injected under pressure. Preferably the modular cement mantle includes at least two ribs positioned on the outside surface which contact the surface of the acetabulum upon implantation to allow for the pressurized application of a uniform layer of bone cement into the acetabulum. The modular cement mantle may also include a plurality of standoff bodies positioned on its inner surface to allow for the application of a uniform layer of bone cement between the inner surface of the modular cement mantle and the outer surface of the implant. One great advantage of the modular cement mantle is that it is "preformed", i.e. fabricated outside the body, preferably in the factory, and consequently is inherently stronger than a cement mantle polymerized in situ. The inventive modular cement mantle also prevents direct impingement of the prosthetic component against the surface of the acetabulum, thereby minimizing fragmentation and loosening of the implant. Moreover, the thickness of the modular cement mantle matches the minimum allowable separation between the prosthesis and the reamed acetabulum, preferably about 3.0 mm.

In a second embodiment, the preformed modular mantle is formed of a bone growth inducing agent. Once inserted into the socket, the modular mantle facilitates bony attachment of the prosthetic implant assembly into the socket. Exemplary bone growth inducing substances include bone grafts, hydroxyapatite, and other osteoinductive materials such as various types of bone growth factors and bone extracts.

In certain embodiments, the inventive modular preformed mantle further includes a relatively simple means for attachment onto the outer surface of an implant. Preferably, the inner surface of the modular mantle comprises a groove which is configured to receive a detent positioned on the outer surface of the prosthetic implant. When the implant is pushed into the modular mantle, the resulting inward resilient compression of the detent against the inner surface of the modular mantle allows for the detent to snap or lock into the groove. The modular mantle may also include at least one hole through which a screw, for example, may be engaged to penetrate the underlying acetabulum and thereby mechanically secure the modular mantle to the acetabulum.

The inventive modular preformed mantle may be used with conventional two-component systems (e.g. outer metal acetabular shell and inner polymeric liner) without modification to the implants employed. This increases the versatility of the metal prosthesis and reduces the range of components which need to be stored within the operating suite. The inventive modular mantles may also be used with conventional one-component systems (i.e. polymeric prosthetic shells). Moreover, through the supply of a range of modular mantle shells of different wall thicknesses, it is also possible to reduce the range of sizes of metal and polymeric prostheses needed at surgery, thereby further reducing the size and cost of the surgical inventory.

The inventive modular preformed mantle has the added advantage that it may have locking features that allow its fixation to a polymeric liner (one-component system) as well as the outer metal shell in the two-component system. The dimensions of the locking features on the modular mantle match those present in the metal shell originally designed to mate with the liner, and therefore is like a replica of the metal shell. This is an attractive feature for manufacturing purposes since manufacturers of different metal shells can quickly adapt to the inventive one-component system using the inventive modular mantle by molding or machining replicas of their metal shells out of (PMMA), for example, or other material used to form the modular mantle. Because of this replication, a manufacturer can be assured that the modular mantle will interlock reliably with its polymeric liner without extensive product development.

In another embodiment of the present invention, the inventive prosthetic implant system may be mechanically affixed directly into the bone socket without the use of a modular preformed mantle. Instead, the implant shell is further affixed to the socket by means of a grout of bone growth inducing substance such as that used in the manufacture of the preformed mantle discussed above. Preferably the implant shell has an apical port through which the bone growth inducing substance may be injected via a syringe, for example, into the shell/socket interspace.

BRIEF DESCRIPTION OF THE FIGURES

FIG. 2 is an exploded view of the components of the one-component prosthetic system in combination with the modular cement mantle.

FIG. 3A is an elevational section of the prosthetic system showing a modular cement mantle with a relatively small wall thickness.

FIG. 3B is an elevational section of the prosthetic system showing a modular cement mantle with a relatively large wall thickness.

FIG. 7 is an exploded view of the components of the two-component prosthetic implant system in combination with the modular cement mantle.

DETAILED DESCRIPTION OF THE PREFERRED EMBODIMENT(S)

The present invention is directed, in certain embodiments, to a modular prosthetic system comprising a modular preformed mantle used to secure an implant, preferably a prosthetic acetabular cup or shell, within a bone socket, preferably an acetabulum. As discussed in more detailed below, the modular mantle may be formed of a polymeric adhesive material (i.e. cement) or a bone growth inducing substance. For ease of explanation, the present invention is described with reference to hip prostheses; however, it is contemplated that one of ordinary skill in the art, having the benefit of this invention's teachings and suggestions, will be able to employ the present invention in other orthopedic applications requiring affixation of prosthetic implants into joint surfaces, including those present in the knee, the shoulder, and the ankle joints, for example.

The phrases "modular mantle" and "modular preformed mantle" used herein refer generally to the inventive modular mantle that has been fabricated outside the body, most preferably in the factory, and thus is "preformed" prior to use in surgery. The phrase "modular cement mantle" refers specifically to the inventive modular mantle formed of a polymeric adhesive material, as discussed in more detail below. The term "cement mantle" refers to the inventive modular cement mantle in combination with the bone cement which has subsequently polymerized in situ during surgery. The phrase "bone fixation mantle" refers to a mantle comprising a bone growth inducing material applied between the bone socket and the outer implant shell, either alone or in combination with a film comprising a bone growth inducing substance precoated on the outer surface of the implant shell.

The phrase "prosthetic component" as used herein refers to any device designed for implantation into a bone socket, including but limited to the implant shells (5,6) as described below and illustrated in the figures as well as the inventive modular preformed mantles.

Figure 1:
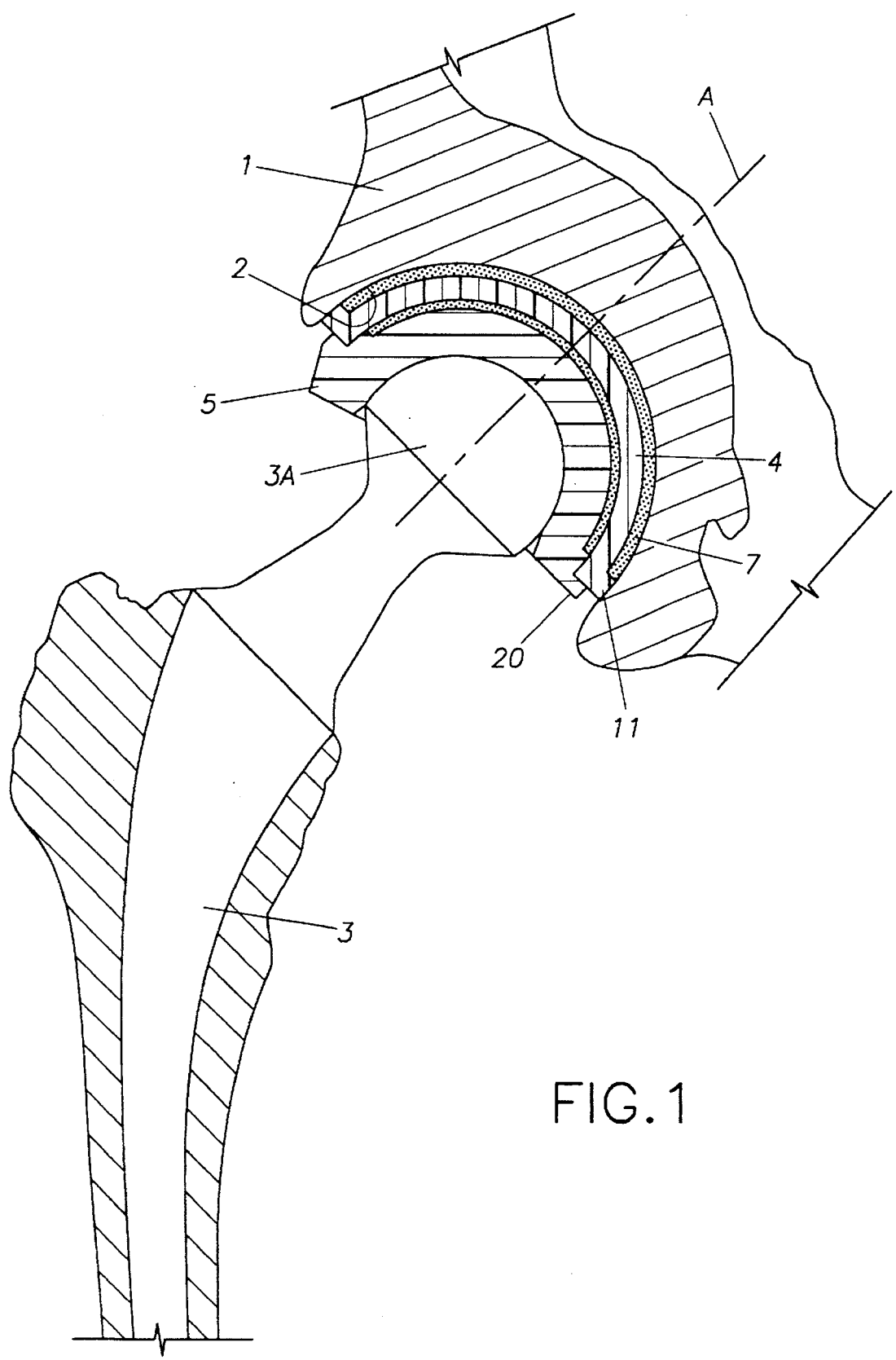
FIG. 1 is an elevational section view of a prosthetic hip joint showing a femoral component mated with a one-component prosthetic system in combination with one embodiment of the modular cement mantle having no special locking features.
Figure 1A:
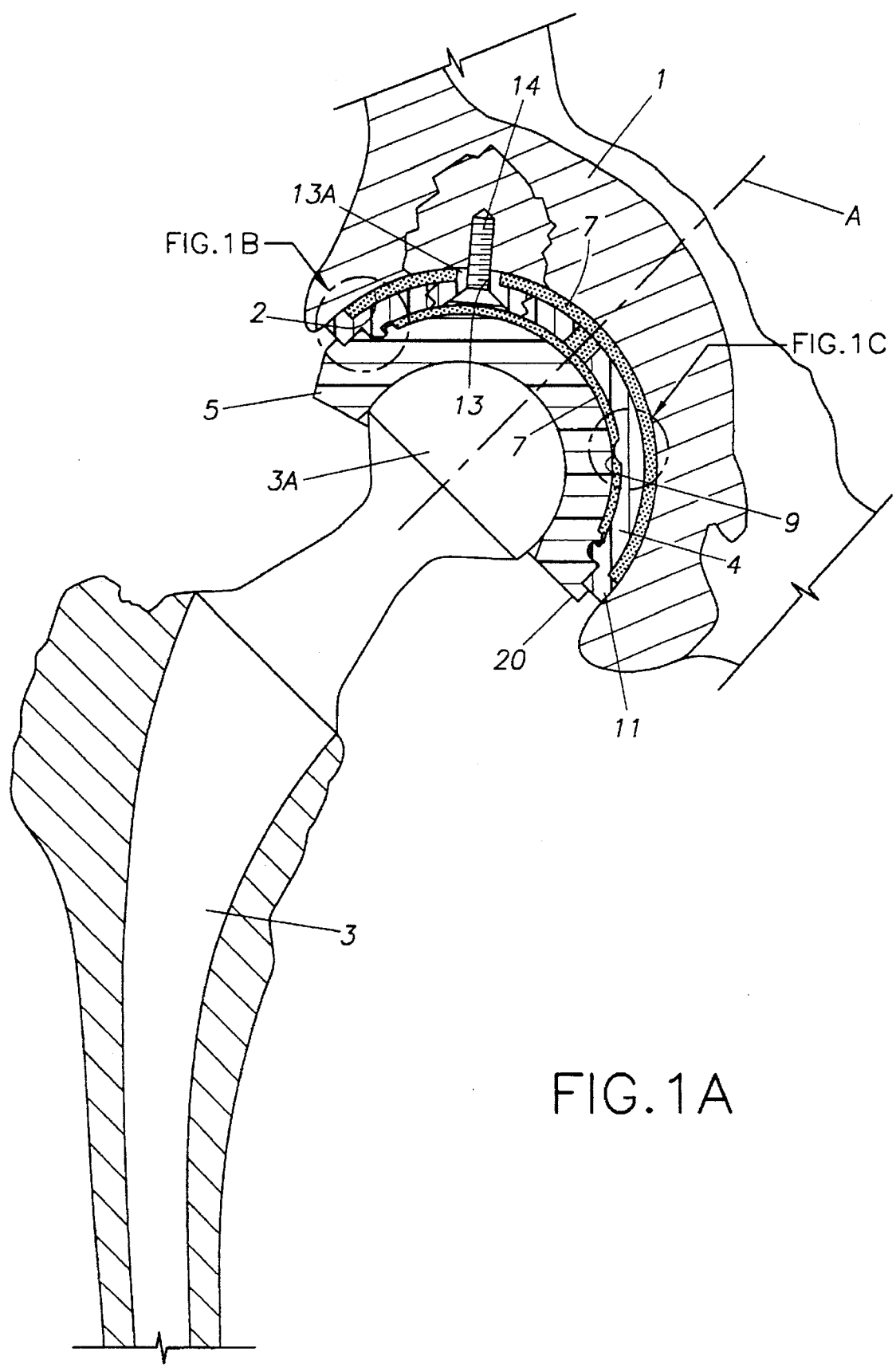
FIG. 1A is an elevational section view of a prosthetic hip joint showing a femoral component mated with a one-component prosthetic system in combination with a second embodiment of the modular cement mantle comprising special locking features.
Figure 1B:
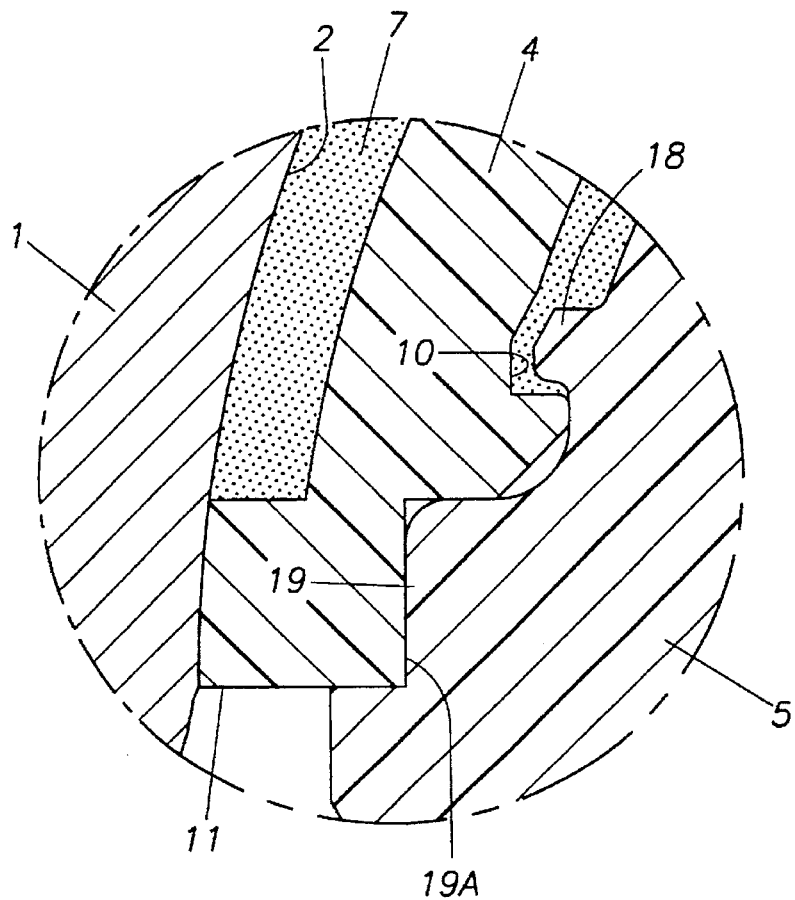
FIG. 1B is a magnified view of the special locking features of the modular cement mantle and implant illustrated in FIG. 1A.
Figure 2A:
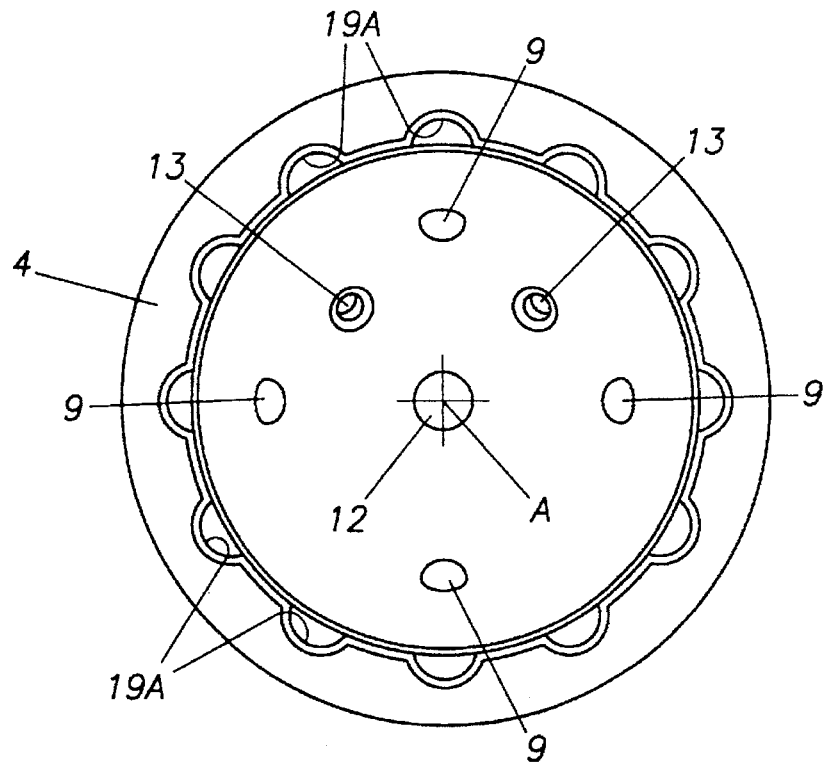
FIG. 2A is bottom plan view of the modular cement mantle taken along lines 2A—2A of FIG. 2.

Referring now to FIGS. 1–5, one embodiment of the present invention comprises a modular cement mantle (4) which is attached to single acetabular implant (5). The implant (5) is preferably formed of a polymeric material such as ultra high molecular weight polyethylene (UHMWPE). [As discussed further below, the implant (5) may be used as the inner polymeric liner in the two-component system which employs an outer metal shell (see FIGS. 6–10).] FIGS. 1 and 1A illustrate the assembled one-component prosthetic system upon implantation within the acetabulum and in combination with a femoral component (3A). In this embodiment, the inventive prosthetic system comprises a modular cement mantle (4) which is preferably hemispherically shaped to conform to the surface of the acetabulum (2) of the pelvis (1) and the outer surface of the implant (5). The modular cement mantle may be formed of any conventional adhesive polymeric material typically used in the art, most preferably polymethylmethacrylate (PMMA), for example. As shown in FIGS. 1A, 2, and 2A, the modular cement mantle may include one or more holes (13) for receiving a screw (14) or other suitable fastener means which penetrates the bone of the acetabulum to secure mechanically the modular cement mantle to the acetabulum. Preferably about each hole (13) is a raised annular ring (13a) which functions to prevent deformation or fracture of the modular preformed mantle when the screw is tightened down within the hole (13). The screw (14) may be formed of a polymeric or metallic material.

The modular cement mantle (4) most preferably includes an apical port (12) through which the liquid bone cement (7) may be injected. After the modular cement mantle has been mechanically secured to the acetabulum as described above, bone cement (7) may be injected under pressure (via a syringe (21), for example) into the acetabulum (2) through the port (12) (see FIG. 4). Conventional liquid bone cements may be employed, including, but not limited to, polymethylmethacrylate (PMMA). The outer surface of the modular cement mantle may also include at least two elevated ribs (8), as shown in FIG. 2. The ribs function to pressurize the cement, control the flow of the cement, stiffen the modular cement mantle, ensure that unfilled areas of the mantle are eliminated, and help to maintain a minimum cement mantle thickness. [The modular mantle preferably has a lower rim or lip (11) which aids in maintaining the liquid bone cement within the modular mantle/socket interface as well as aid in the pressurization of the bone cement therein.] Once the bone cement has been applied, the cement is allowed to polymerize.

After the modular cement mantle (4) is secured within the acetabulum as described above, the implant (5) is inserted into the inner surface of the modular cement mantle. Preferably, the implant has a lower lip (20) that is configured to mate with the lower rim (11) of the modular mantle upon assembly of the two components within the socket. This design is particularly advantageous when an intermediary layer of bone cement is applied between the modular mantle and implant, as shown in FIGS. 1 and 1A and discussed in more detail below.

The inner bearing surface of the implant (5) is configured to complement the head (3a) of the prosthetic femoral stem (3) to engage the femoral head therein. Prior to engaging the implant within the modular cement mantle, a facsimile (not shown) of the implant which does not engage the locking features of the implant is placed within the modular cement mantle in order to determine the preferred orientation of the implant within the modular cement mantle. During this procedure, the head (3a) of the femoral component is mated with the facsimile, and the resulting artificial joint is moved to its extremes of motion to determine whether it will provide adequate excursion without dislocation or instability. In the event that insufficient motion is present, the implant may be rotated within the modular cement mantle, or the implant may replaced with another implant of a different design in order to increase the amount of stable motion. As shown in FIGS. 2, 3A, and 3B, for example, the lower edge of the implant preferably includes two second lips (25) extending downward at an angle, preferably from about 10° to about 20°, to provide increased stability to the prosthetic joint at its extremes of motion. As discussed in more detail below, once the desired orientation of the implant is determined, the appropriate implant is selected and positioned within the modular cement mantle accordingly.

Figure 1C:
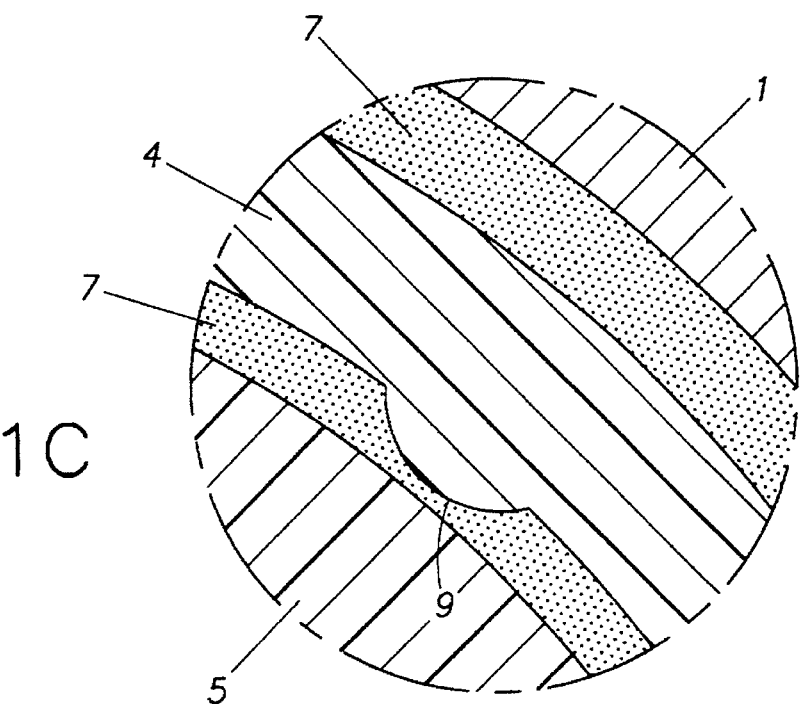
FIG. 1C is a magnified view of a standoff body present on the inner surface of the modular cement mantle illustrated in FIG. 1A.
Figure 5:
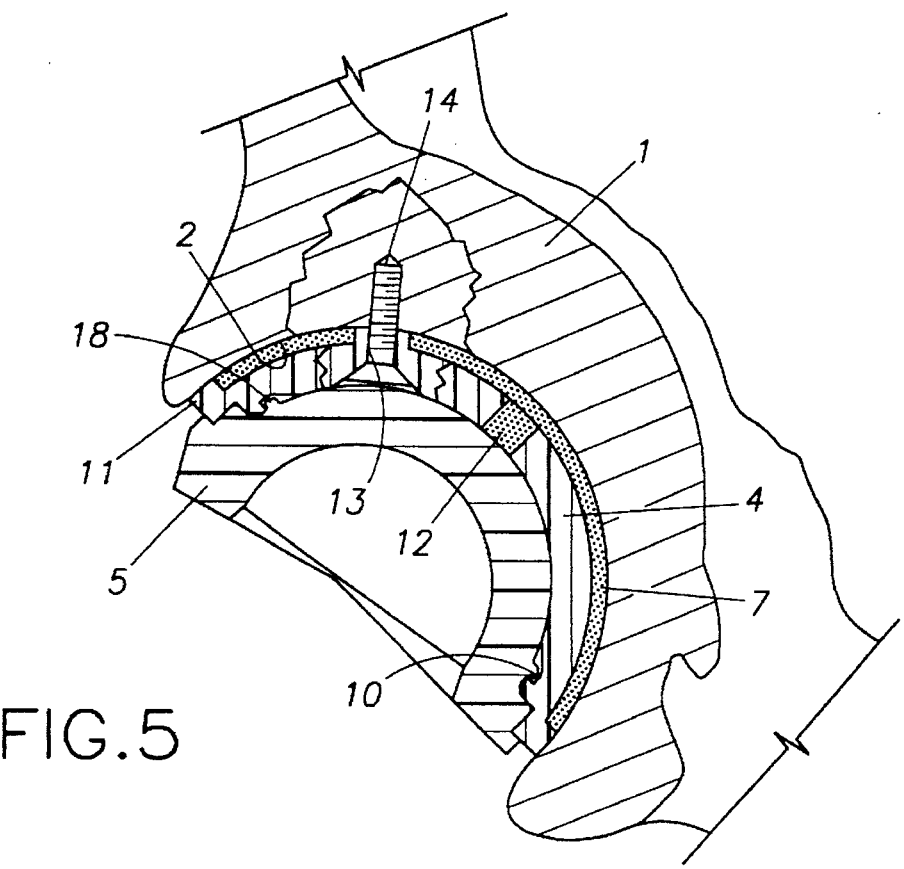
FIG. 5 is a sectional view of an acetabular implant component mated to the modular cement mantle by mechanical means only (i.e. no intermediary layer of bone cement).

As shown in FIGS. 1 and 1A, a layer of bone cement (7) may be applied to the inner surface of the modular cement mantle (4) prior to attachment of the implant (5). The lower lip (20) of the implant (5) functions in part to maintain the intermediary layer of bone cement within the gap during polymerization. In this embodiment, it is more preferable that the modular cement mantle have at least two standoff bodies (9) extending from its inner surface to allow for the application of a uniform layer of bone cement, as illustrated in FIG. 1A. As shown in FIG. 1C, the standoff bodies preferably do not completely bridge the gap between the modular cement mantle and the implant. Alternatively, the implant (5) may be attached to the modular cement mantle (4) without an intermediary layer of bone cement, as illustrated in FIG. 5. Providing an intermediary layer of bone cement, however, is advantageous since it diminishes the likelihood of any relative motion between the modular cement mantle and the implant which consequently may generate abrasive debris of polymer and acrylic, thereby potentially leading to osteolysis and loosening.

As shown in FIGS. 1A, 1B, 2, and 2A, for example, the implant (5) is snapped or locked into place by means of a detent (18), preferably an interrupted annular detent, positioned on the outside surface of the implant which is received within a groove (10), preferably an annular groove, positioned on the inner surface of the modular cement mantle. When the implant is pushed into the modular cement mantle, the resulting inward resilient compression of the detent (18) against the inner surface of the modular mantle allows the detent to snap or lock into place within the groove (10) to prevent the implant from disengaging from the modular cement mantle. Preferably, the detent (18) is angled or hemispherically-shaped, thus allowing it to slide more easily into the groove (10). While the foregoing locking mechanism is preferred in the present invention, other conventional methods or devices suitable for attaching the implant to the mantle may be employed. Alternatively, the modular cement mantle may contain no mechanical locking features for attachment to the implant, as shown in FIG. 1, for example, thus relying on friction and/or an intermediary layer of bone cement for securement thereto.

As discussed above, the preferred orientation of the implant (5) is determined prior to locking it within the modular cement mantle (5). When the desired orientation of the implant about axis (A) is determined, the implant is locked into the modular cement mantle by means of a series of detents (19) integral with the outer surface of the implant as shown in FIG. 2, each of which are configured to complement and engage a corresponding notch (19A) positioned within the inner surface of the modular cement mantle, as shown in FIG. 2A. The inventive prosthetic system preferably includes a plurality of such detents (19) and notches (19A) to allow for a wider range of positions within the modular cement mantle along axis (A). Once the implant is "dialed" into the desired positioned, it is pushed into the modular cement mantle to engage the detents (19) within the corresponding notches (19A), thereby preventing any further rotational movement (i.e. about axis (A)) of the implant within the modular cement mantle. While the foregoing mechanism for preventing rotational movement of the implant within the mantle is preferred, other conventional locking devices or methods may be employed, as well. Alternatively, such features for preventing this kind of rotation may be eliminated entirely in cases where post surgical rotational movement of the implant is not a concern.

The same polymeric implant (5) may be fixed in acetabula of different inner diameters by selecting modular cement mantles of different thicknesses, as illustrated in FIGS. 3A and 3B. FIG. 3A illustrates a modular cement mantle (4) having a relatively small thickness ($T_1$) (preferably about 2.5 mm), and FIG. 3B illustrates a modular cement mantle (4) having a relatively large thickness ($T_2$) (preferably about 5.5 mm). Preferably, the inventive modular cement mantle should have a minimum thickness of from about 2.5 to 3.0 mm. The thinner modular cement mantle (FIG. 3A) is more preferred over the thicker modular cement mantle (FIG. 3B) in that the former allows the polymeric implant to have a greater wall thickness, thus reducing the wear rate of the plastic surface. Nevertheless, by having on hand several modular cement mantles of varying thickness during surgery, the number of more costly implant shells, particularly metal shells (as discussed in more detail below) is reduced, thereby minimizing the overall cost of the prosthetic system.

Referring now to FIGS. 6-10, a second embodiment of the present invention includes a two-component prosthetic system preferably comprising a metal shell component (6) and an inner polymeric liner (5). [While the preferred materials for forming the shell (6) and liner (5) are metals and polymers, respectively, it is within the scope of the present invention that other suitable materials, either presently used or later discovered, for use in orthopedic applications may be employed instead.] As discussed above, the polymeric liner (5) may be formed of the same material as, and configured similarly to, the implant of the one-component system. In this second embodiment, the metal shell (6) is preferably hemispherically shaped to complement the inner surface of the modular cement mantle (4). As illustrated in FIG. 7, holes (13, 16) may be present within the metal shell and the modular cement mantle, respectively, to receive a fastener means, preferably a screw (14), which penetrates the bone of the acetabulum (2) to secure mechanically both the modular cement mantle and the metal shell to the acetabulum. The screw (14) is preferably formed of the same materials as discussed above for the one-component prosthetic system.

After the modular cement mantle (4) and the metal shell (6) have been mechanically secured within the acetabulum (2), a layer of bone cement (7) is then injected, preferably under pressure, through the apical port (15) of the metal shell and the apical port (12) of the modular cement mantle, both ports being aligned coaxially (see FIGS. 6 and 8). [Alternatively, the liquid bone cement may be delivered under pressure with only the modular cement mantle attached to the acetabulum, especially if multiple screws are present.] As for the one-component prosthetic system, the modular cement mantle preferably includes at least two ribs (8), more preferably from about three to about six ribs, which extend from the outer surface of the modular cement mantle and directly contact the acetabulum (2) to allow for the application of a uniform layer of bone cement, as shown in FIG. 7, for example. Once the desired amount of the bone cement has been injected into the acetabulum, the continual injection of bone cement through the apical port (15) of the metal shell results in a pressurized application of bone cement into the gap between the modular cement mantle and the metal shell (primarily when only one apical port is present). This gap (as shown, for example, in FIGS. 6 and 8, containing liquid cement (7)) is created by the standoff bodies (9) of the modular cement mantle which allow for the application of a uniform layer of bone cement therein.

Figure 8:
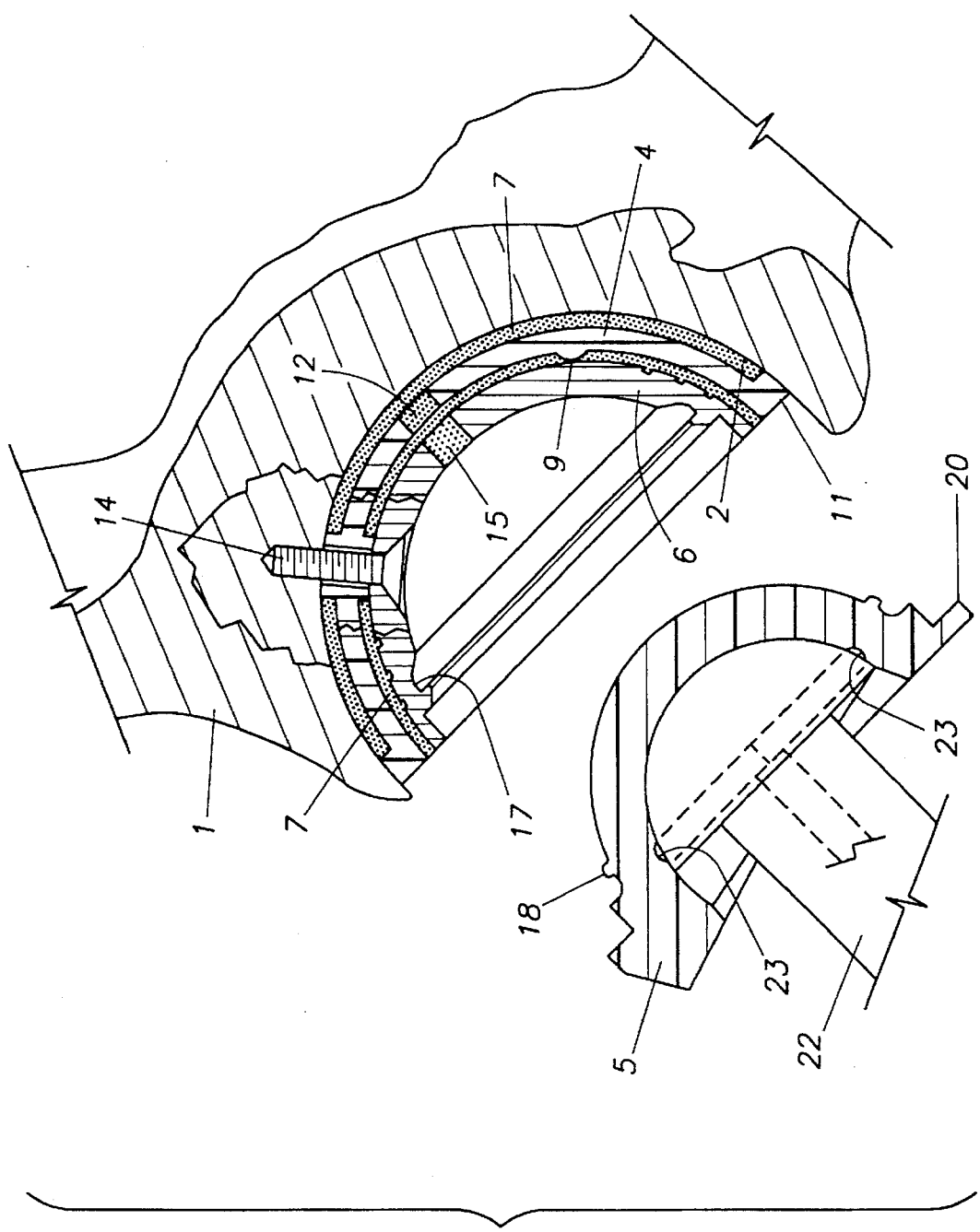
FIG. 8 is a sectional view of a modular cement mantle and an outer metal shell affixed to the acetabulum. The inner polymeric liner is shown being installed by means of an insertion tool.

Next, the polymeric liner (5) is inserted into the metal shell (6), preferably prior to the polymerization of the liquid bone cement (7). [As discussed above for the one-component system, the liner (5) preferably has a lower lip or rim (20) that is configured to mate with the lower rim (11) of the modular mantle upon assembly of the components within the acetabulum, and thereby serves in part to maintain any intermediary layer of bone cement applied between the liner and metal shell.] FIG. 8 illustrates one means for inserting the polymeric liner into the metal shell using an insertion tool (22) which is attached to the inner surface of the polymeric liner via a keyway (23) contained within the liner. The proper orientation of the polymeric liner within the metal shell may be ascertained by the same procedure as described above for the one-component prosthetic system. Once the desired orientation is determined, the liner (5) may be snapped or locked into place by means of a detent (18), preferably an annular detent, positioned on the outside surface of the implant which is received within a groove (17), preferably an annular groove, positioned on the inner surface of the metal shell. When the implant is pushed into the metal shell, the resulting inward resilient compression of the detent (18) against the inner surface of the metal shell allows for the detent to snap or lock into place within the groove. As for the inventive one-component prosthetic system described above, the detent (18) is preferably angled or hemishperically-shaped, thus allowing it to slide more easily into the groove (17). As discussed above for the one-component prosthetic system, other conventional methods or devices suitable for attaching the polymeric liner to the metal shell may be employed. Furthermore, other types of liners generally known by those of ordinary skill in the art may be employed, as well.

Figure 7A:
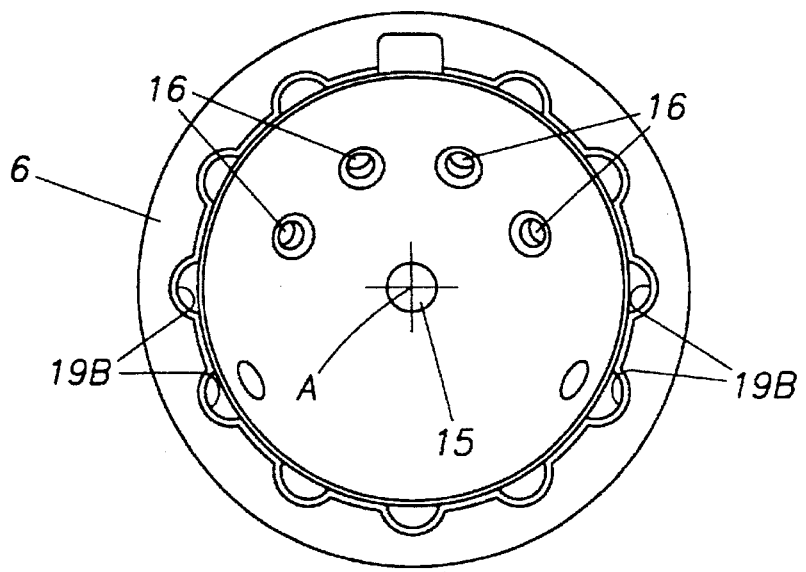
FIG. 7A is a bottom plan view of the outer metal acetabular shell taken along lines 7A—7A of FIG. 7.
Figure 4:
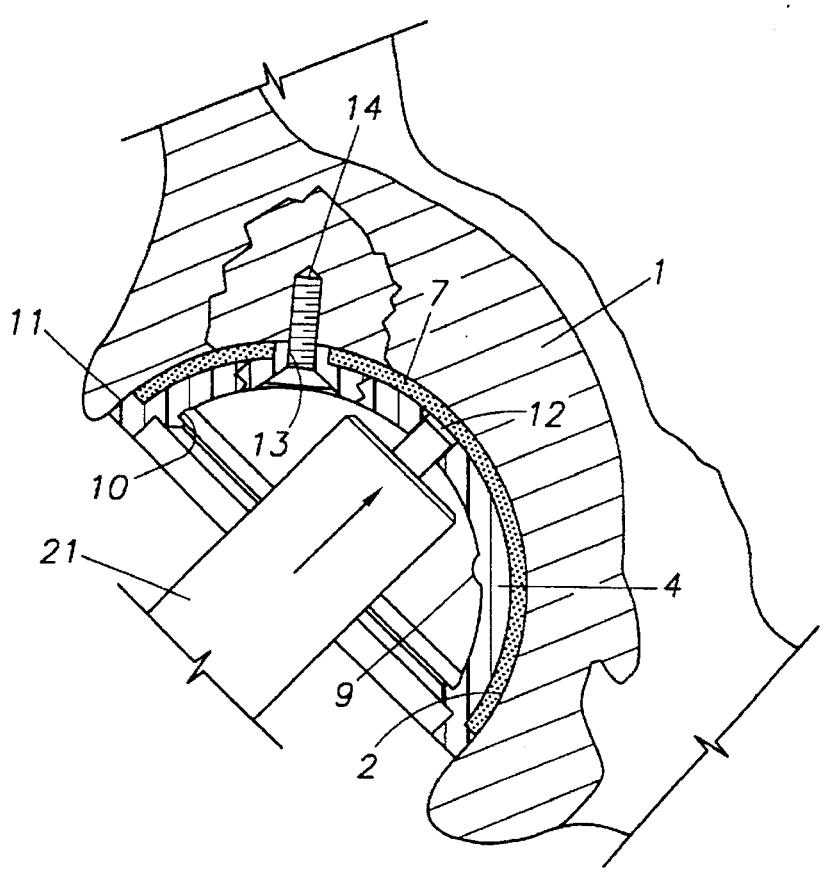
FIG. 4 is sectional view of a modular cement mantle affixed to the acetabulum by a screw as bone cement is injected into the acetabulum via a syringe.
Figure 6:
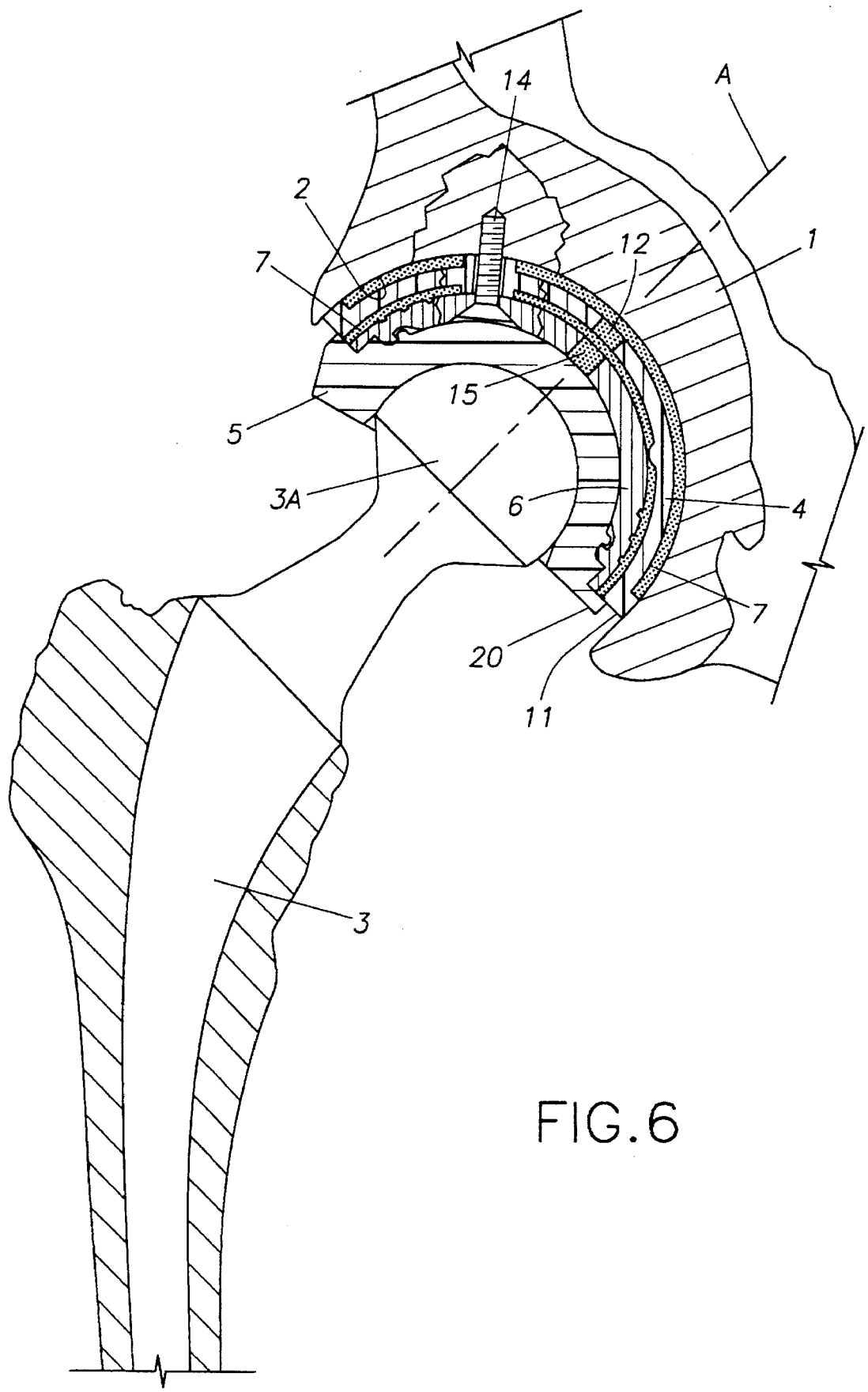
FIG. 6 is an elevational section view of a prosthetic hip joint showing a femoral component mated to a two-component prosthetic implant system in combination with the modular cement mantle.

Similarly, the outer surface of polymeric liner (5) preferably comprises a series of detents (19), as shown in FIG. 7, designed to complement and engage a corresponding notch (19B) positioned within the inner surface of the metal shell (6) (FIG. 7A). This combination of detents and notches allows for a wider range of rotational positions with respect to the pelvis (1) (i.e. about the axis (A) as illustrated in FIGS. 6 and 7A, for example). Once the liner (5) is dialed (i.e. rotated) into the desired position, the liner is pushed into the metal shell to engage the detents (19) within the corresponding notches (19B), thereby preventing any further rotational movement about axis (A) of the liner within the metal shell. As discussed above for the one-component prosthetic system, other conventional locking devices or methods may be employed, as well. Alternatively, such features for preventing this kind of rotation may be eliminated entirely in cases where post surgical rotational movement of the implant is not a concern.

Figure 10:
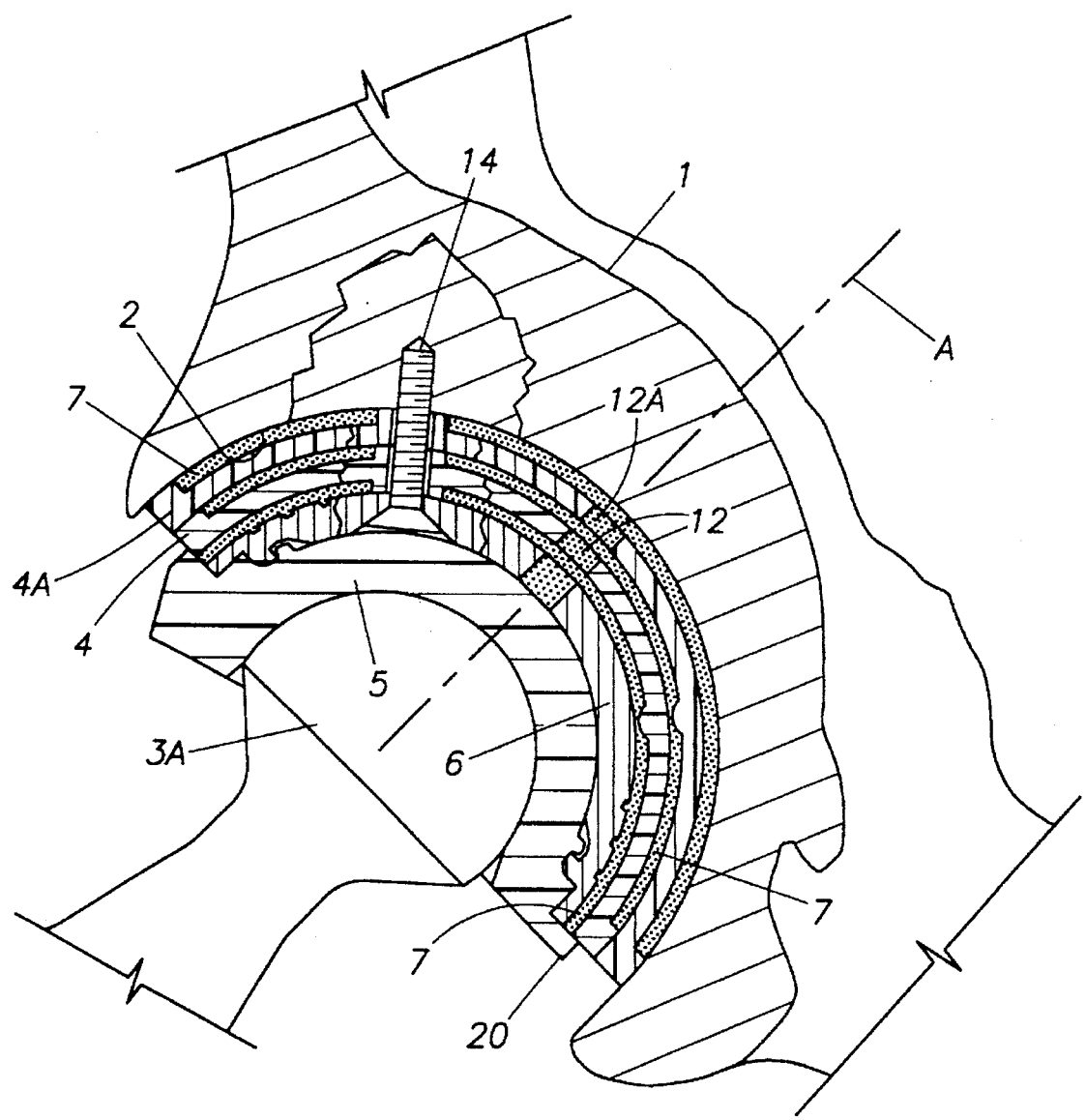
FIG. 10 is a sectional view illustrating a two-component prosthetic implant system in combination with two separate modular cement mantles.

In addition to, or in lieu of, using a modular cement mantle of a particular thickness, as discussed in the preceding paragraph, more than one modular cement mantle may be used to secure a prosthetic implant system into a particular bone socket. FIG. 10 illustrates the use of two modular cement mantles (4 and 4a) in combination with a two-component prosthetic implant system described herein. [The one-component system may employ a plurality of modular cement mantles, as well.] Preferably, a layer of bone cement (7) is applied between the adjacent modular cement mantles (4, 4a). In this embodiment, all of the modular cement mantles used may be designed as illustrated in FIGS. 1A and 2, for example, to include locking features, or may be designed very simply without any locking features, as illustrated in FIGS. 1 and 10, for example. Moreover, the modular cement mantles, in particular those not in direct contact with the bone socket (i.e. 4a), may exclude standoff bodies (9) and/or ribs (8).

The metal shell (6) is preferably formed of conventional metals and metal alloys used in orthopedic applications and include, but are not limited to biocompatible alloys of cobalt and titanium. Similarly, the polymeric liner (5) is preferably formed of conventional bearing materials used in orthopedic applications, preferably in hip prostheses, including, but not limited to, ultra high molecular weight polyethylene (UHMWPE). As discussed previously, the shell (6) and liner (5) may be formed of other materials currently used by those of ordinary skill in the art in various orthopedic applications or materials that are later discovered suitable for use in orthopedic applications.

As discussed above, the inventive modular cement mantle may be used with one-component and modular two-component prosthetic systems described herein as well as other modular prosthetic implant systems employing one or more implants containing different, if any, locking mechanisms. Moreover, in both the one-component and two-component prosthetic systems, the modular cement mantle is most preferably in the shape of a full hemisphere, and consequently is capable of enclosing all or a substantial portion of the outer surface of the prosthetic component, as illustrated in the figures. However, other types of modular cement mantles having different configurations are within the scope of the present invention. Such alternative embodiments include, but are not limited to, those modular cement mantles in the form of a circumferential ring or in the form of a partial hemisphere.

The method of implanting the inventive one-component prosthetic system in combination with a preformed cement mantle (see FIGS. 1-5) includes first reaming the acetabulum (2) to a desired depth. A series of holes (not shown) are then drilled into the acetabular surface to facilitate interdigitation of the liquid acrylic cement. The reamed socket is then irrigated with a pulsatile lavage system to remove blood, fat, and particles of bone that may occlude the natural porosity of the exposed bony surface. Next, the cement is delivered into the acetabulum, preferably by using a cement gun (not shown) with a nozzle capable of fitting tightly into each of the anchorage holes to allow pressurization of each hole.

Additional cement is delivered into the socket to form a layer between the modular cement mantle (4) and the bony surface. Next, the modular cement mantle is fitted within the acetabulum and secured mechanically, more preferably by means of a polymeric screw, as described above. The liquid cement (7) between the modular cement mantle and the acetabulum is pressurized by injecting additional cement through an apical port (12) contained within the modular cement mantle. Once the liquid cement has been pressurized for about 10 to about 20 seconds, the cement syringe (21) is disengaged from the modular cement mantle, and additional cement is extruded into the hemispherical cavity formed by the modular cement mantle. Next, an acetabular implant component, preferably one of the types described herein, is secured within the inner surface of the modular cement mantle. As discussed above, the desired orientation of the acetabular implant is first determined, preferably with a facsimile which does not engage the locking features of the modular cement mantle, prior to the cementing procedure.

Alternatively, the modular cement mantle and the polymeric liner may be preassembled prior to implantation (not shown). Here, a layer of liquid bone cement is either applied onto the outer surface of the modular cement mantle or directly into the acetabulum. Next, the preassembled system is inserted into the acetabulum. This method for implanting the inventive one-component prosthetic system is not as preferred because the bone cement is not applied under pressure, and the assembly is not mechanically secured to the acetabulum, thereby resulting in the possibility of malpositioning during implantation.

For implanting a two-component prosthetic system within the acetabulum, preferably a metal shell/polymeric liner system such as that described herein, for example, the acetabulum (2) is first reamed to the desired depth. As discussed above for the one-component system, a series of holes (not shown) are then drilled into the acetabular surface to facilitate interdigitation of the acrylic cement. The reamed socket is then irrigated with a pulsatile lavage system to remove blood, fat, and particles of bone that may occlude the natural porosity of the bony surface. Next, the liquid cement (7) is delivered into the acetabulum, preferably by using a cement gun (not shown) with a nozzle capable of fitting tightly into each of the anchorage holes to allow pressurization of each hole. Additional liquid cement is delivered into the socket to form a layer between the modular cement mantle and the bony surface. Next, the modular cement mantle is fitted within the acetabulum and secured mechanically, more preferably by means of a metal or polymeric screw, as described above. The cement between the modular cement mantle and the acetabulum is pressurized by injecting additional cement through an apical port (12) contained within the modular cement mantle. Once the liquid cement has been pressurized for about 10 to about 20 seconds, the cement syringe is disengaged from the modular cement mantle, and additional cement is extruded into the hemispherical cavity formed by the modular cement mantle.

After the modular cement mantle (4) is positioned within the acetabulum, the metal shell (6) is mated within the inner surface of the modular cement mantle. The combination modular cement mantle/metal shell is mechanically engaged within the acetabulum (2) preferably by inserting a screw (14) through these components and into the acetabulum, as described previously. Preferably, a sufficient amount of liquid bone cement (7) is then injected into the underlying acetabulum, under pressure, though the coaxial ports (12, 15) contained within the modular cement mantle and the metal shell, respectively. Next, the desired orientation of the polymeric liner (5) is determined, preferably with a facsimile which does not engage the locking features of the metal shell, prior to locking the polymeric liner within the metal shell, as described previously. FIG. 8 illustrates one means for inserting the polymeric liner into the metal shell via an insertion tool (22) which is secured within the polymeric liner by engaging keyways (23) contained within the inner surface of the liner.

While the foregoing method of implantation of the two-component prosthetic system is generally the most preferred, an alternative method comprises preassembling the metal shell (6) and the polymeric liner (5) prior to insertion within the modular cement mantle (not shown). Here, the modular cement mantle is mechanically secured within the acetabulum, as described above, and then a layer of bone cement (7) is injected into the acetabulum, under pressure, through a port (12) in the modular cement mantle. Preferably, a second layer of bone cement is then applied to the inner surface of the modular cement mantle. Next, the metal shell and polymeric liner are attached to one another, preferably by the locking means described above, and then are inserted, in combination, into the modular cement mantle. While this method has certain advantages (as discussed further below), one potential disadvantage is that the stability of the hip joint cannot be reliably evaluated prior to implantation of the assembled implant into the modular cement mantle since the metal shell is not further affixed to the modular cement mantle by mechanical means.

Figure 9:
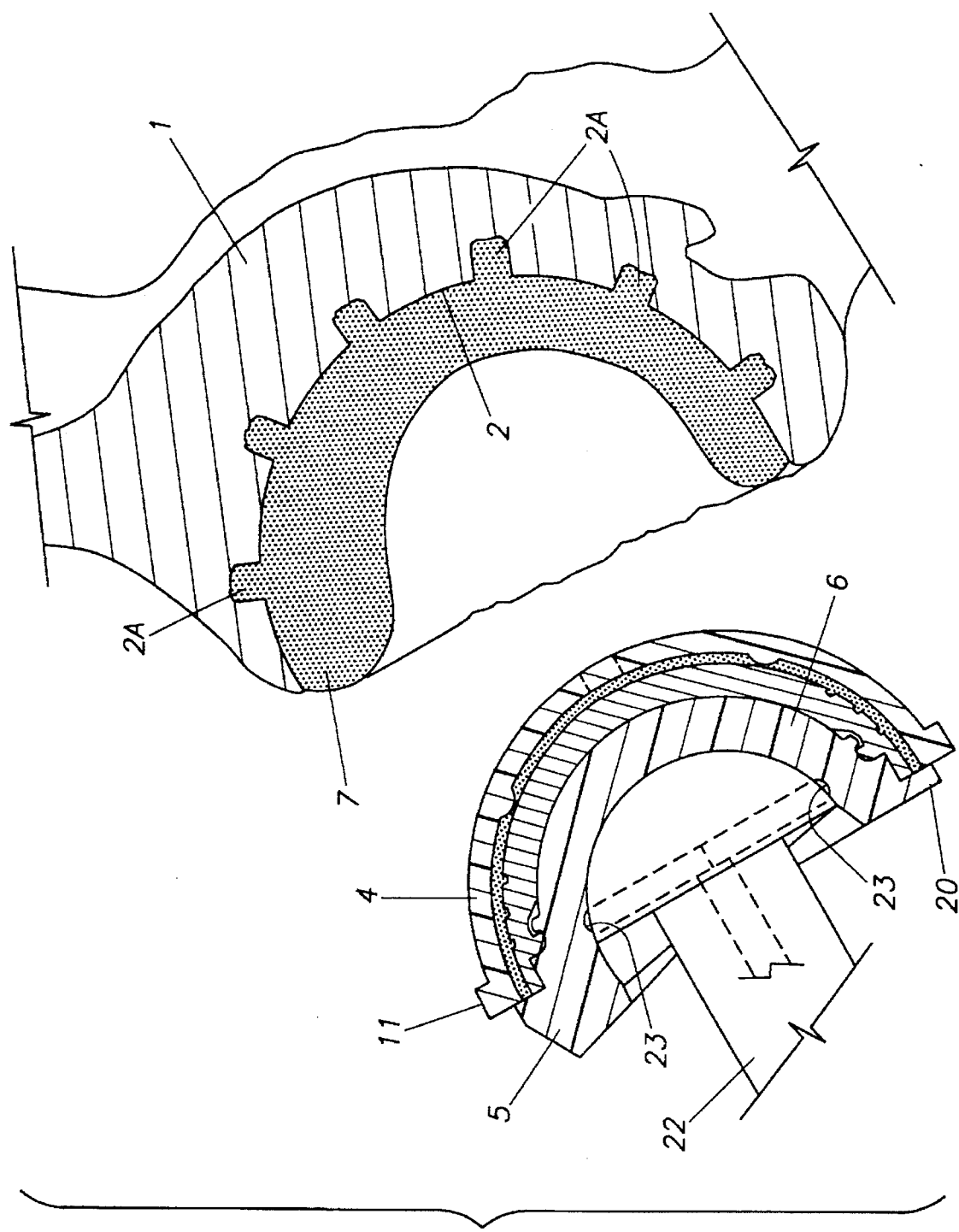
FIG. 9 is a sectional view illustrating installation of a preassembled prosthetic implant system/modular cement mantle into the acetabulum by means of an insertion tool.

A second alternative method for implanting the inventive two-component prosthetic system comprises preassembling the modular cement mantle (4), metal shell (6), and polymeric liner (5) prior to implantation, as shown in FIG. 9. Here, the preassembled components are attached to one another, preferably by the locking features described above, as well as by an intermediary layer of bone cement (7) between the modular cement mantle and the metal shell. The acetabulum (2) is further prepared by drilling holes (2A) into the floor of the acetabulum prior to the application of bone cement to allow the cement to flow therein and thus facilitate fixation. Next, a layer of bone cement (7) is applied directly into the acetabulum, as shown in FIG. 9. The entire prosthetic assembly can then be inserted into the acetabulum by means of an insertion tool (22), for example. In this method, there is an increased risk of loosening of the prosthetic system within the acetabulum due to the lack of (1) mechanical affixation of the assembly to the acetabulum and (2) pressurized application of the bone cement between the outer surface of the modular cement mantle and the acetabulum.

Notwithstanding the aforementioned potential disadvantages, these alternative "preassembled" implantation methods for the two-component prosthetic system have the advantage of being simpler to use because they simulate conventional cementing techniques in which the prepared acetabulum is filled with acrylic cement, and the acetabular cup is implanted as one piece, mounted on an introducer. Preassembling all three components (i.e. the modular cement mantle, metal shell, and polymeric liner) has the potential advantage that, as the acetabulum bleeds and is often contaminated with blood and fat, the prosthetic components may be assembled outside the wound, with or without the use of intermediate layers of liquid cement. In contrast, placement of a modular cement mantle within the acetabulum prior to assembly of the metal shell and liner (or just the liner alone for the one-component prosthetic system) runs the risk that the blood and fat that initially bathe the surface of the modular cement mantle will not be displaced by the wet cement, and consequently will form areas of weakness between the new and preformed modular cement mantle. This latter risk inherent with the most preferred method of sequential implantation of the modular cement mantle, metal shell, and polymeric liner (or modular cement mantle and liner for the one-component system), however, is believed to be outweighed by the benefits afforded by pressurization through the modular cement mantle.

Figure 11:
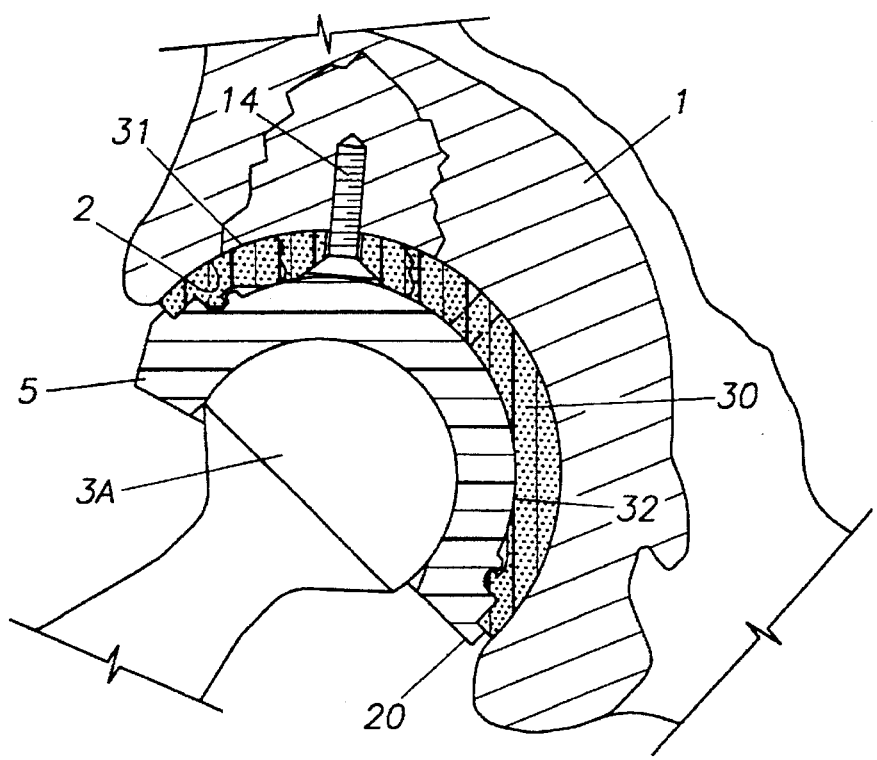
FIG. 11 is a sectional view of a femoral component mated with a one-component prosthetic implant system in combination with a modular preformed mantle formed of a bone growth inducing material.

FIG. 11 illustrates a second embodiment of the inventive modular preformed mantle for use with one- and two-component prosthetic systems. In this embodiment, the modular mantle is formed of a substance comprising a bone growth-inducing agent. Exemplary materials include bone grafts, hydroxyapatite, and other osteoinductive materials, including but not limited to, bone extracts and bone growth factors. Examples of bone growth factors include insulin-like bone growth factors (e.g. IGF-I and IGF-II), transforming growth factor (e.g. $TGF_1$ and $TGF_2$), basic fibroblast growth factor (Basic FGF), acidic fibroblast growth factor (acidic FGF), platelet derived growth factor (PDGF), and bone morphogenetic proteins (e.g. BMP-1, BMP-2, BMP-3, BMP-4, BMP-5, BMP-6 and BMP-7). Other terms synonymous with bone growth factors include Somatomedan C, Skeletal Growth Factor, Cartilage Reducing Factor A, Cartilage Reducing Factor B, BMP-2a, BMP2b, osteogenin, and osteogenic protein-1.

As shown in FIG. 11, the preformed mantle (4) preferably comprises detent/notch locking features (similar to those already described above for the modular cement mantle) for attachment to the prosthetic shell. However, as with the modular cement mantle, the modular mantle formed of a bone growth-inducing agent may employ other conventional attachment means or methods suitable for attaching the modular mantle to the implant. Unlike the modular cement mantle, however, the modular mantle depicted in FIG. 11 does not require an intermediary layer of adhesive or grout of bone growth inducing material between the acetabulum and the modular preformed mantle (4). Instead, the acetabulum may be reamed prior to implantation to a diameter that is less that of the modular mantle, such that the modular mantle may be wedged into the acetabulum and thus maintained tightly therein. Optionally, the modular mantle may be further secured within the acetabulum using at least one screw (14), for example, as shown in FIG. 11, and/or an intermediary layer of bone-growth inducing agent (not shown). Preparation of the acetabulum prior to implantation of the modular preformed mantle and prosthetic implant system is the same as described for the modular cement mantle, except there is no introduction of liquid bone cement between the acetabulum and the modular preformed mantle (although optionally a layer of bone growth inducing material may be applied between the modular mantle and acetabulum.

Figure 12:
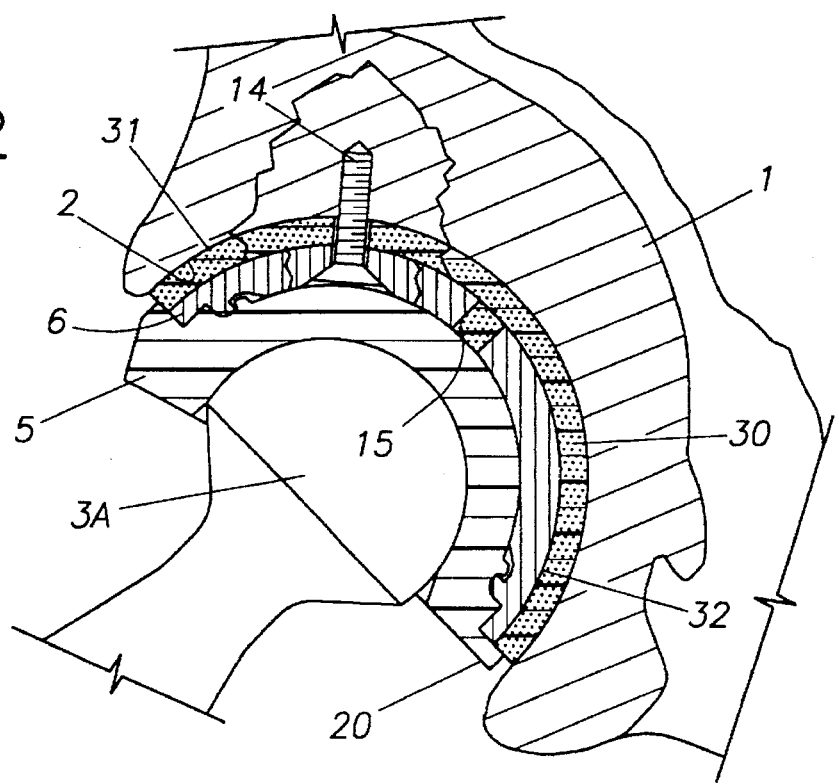
FIG. 12 is an elevational section view of a femoral component mated with a two-component prosthetic implant system in combination with a bone fixation mantle comprising a bone growth inducing material which is injected between the acetabulum/shell interspace.

FIG. 12 illustrates another embodiment of the present invention comprising an outer prosthetic shell (6) that is either textured, chemically treated, or precoated with a film comprising a bone growth-inducing substance (32), for example. Preferably the shell is secured within the acetabulum (2) with at least one screw (14). The shell preferably includes an apical hole (15) through which a bone growth-inducing substance (31) may be injected via a syringe into the space between the acetabulum and the outer surface of the shell after the shell is secured within the acetabulum. FIG. 12 illustrates the final mantle (30) as either the bone growth-inducing material (31) or the combination of injected bone growth-inducing material (31) and a film of bone growth-inducing material precoated (32) on the outer surface of the shell. The outer prosthetic shell in contact with the acetabulum may be either a metal shell, for example, which is commonly used in two-component systems described herein (see FIG. 12), or it may be formed of another material and used alone as a single prosthetic implant (not shown). Suitable materials in the latter case include ceramics, for example, or other materials that are conducive to, or facilitate, bone growth within the acetabulum.

As discussed previously for the modular cement mantle, the modular preformed mantle comprising a bone growth inducing agent may be used in combination with one-component and modular two-component prosthetic implant systems described herein as well as other modular implant systems employing one or more implants containing different, if any, locking mechanisms. Similarly, the modular preformed mantle is most preferably in the shape of a full hemisphere, and consequently is capable of enclosing all or a substantial portion of the outer surface of the prosthetic component, as illustrated in the figures. However, other configurational types of this second embodiment of the inventive modular preformed mantle are also within the scope of the present invention. As discussed earlier for the modular cement mantle, such alternative embodiments include, but are not limited to, those modular mantles in the form of a circumferential ring or in the form of a partial hemisphere.

For implanting the prosthetic system described above and illustrated in FIG. 12, the acetabulum (2) is reamed to the desired depth. Preferably a series of holes are then drilled into the acetabulum surface to facilitate interdigitation of the bone growth inducing substance. The reamed acetabulum is then irrigated as described previously to remove blood, fat, and bone particles. The outer shell (6) is then fitted within the acetabulum (2) and mechanically secured therein with at least one screw (14), for example. Next, a grout of bone growth inducing material (31) is injected through the apical hole (15) of the outer shell and into the space between the acetabulum (2) and outer shell (6). If a two-component prosthetic system is being employed, as shown in FIG. 12, the polymeric liner (5) is then mated within the inner surface of the outer shell (6). As discussed previously, the desired orientation of the polymeric liner (5) is determined, preferably with a facsimile which does not engage the locking features of the shell (6), prior to locking the polymeric liner within the shell.

The foregoing disclosure and description of the invention are illustrative and explanatory thereof, and changes in the size and shape of the inventive prosthetic components described herein, and materials, as well as in the details of the illustrated construction may be made without departing from the spirit of the invention. Accordingly, the scope of the present invention should be determined only by the claims appended hereto.

We claim:

1. A modular cement mantle suitable for securing one or more prosthetic components into a bone socket of a joint, said modular mantle comprising an outer surface configured to complement a bone socket of a joint and an inner surface configured to complement a prosthetic component.

2. The modular cement mantle of claim 1, wherein said modular mantle further includes at least one port through which a bone cement may be injected into said bone socket.

3. The modular cement mantle of claim 2, wherein said outer surface further includes at least two ribs integral with, and extending from, said outer surface.

4. The modular cement mantle of claim 1, wherein said inner surface further includes at least one standoff body integral with, and extending from, said inner surface.

5. The modular cement mantle of claim 1, further including a means for securing said modular mantle to said prosthetic component.

6. The modular cement mantle of claim 5, wherein said means for securing said modular mantle to said prosthetic component includes a groove positioned within said inner surface of said modular mantle and configured to receive a detent positioned on an outer surface of said prosthetic component.

7. The modular cement mantle of claim 5, wherein said means for securing said modular mantle to said prosthetic component further includes a means for preventing rotational movement of the prosthetic component within the modular mantle.

8. A modular prosthetic system for implantation into a mammalian bone socket of a joint, said system comprising:
a first prosthetic implant having an outer surface and an inner surface; and
a modular mantle having an outer surface and an inner surface, wherein said inner surface of said modular mantle is configured to complement said outer surface of said first implant, and said outer surface of said modular mantle is configured to complement said bone socket of a joint.

9. The system of claim 8, wherein said modular mantle is formed of a polymeric material.

10. The system of claim 9, further including a means for securing said modular mantle to a bone socket, said securing means including a layer of bone cement applied to said outer surface of said modular mantle.

11. The system of claim 10, wherein said means for securing said modular mantle to a bone socket further includes a fastener engaged within each of at least one hole communicating through said modular mantle.

12. The system of claim 8, wherein said modular mantle is formed of a bone growth inducing substance.

13. The system of claim 8, and further including a means for securing said first implant to said modular mantle.

14. The system of claim 13, wherein said means for securing said modular mantle to said first implant includes a detent integral with, and extending from, the outer surface of the first implant, and a groove contained within the inner surface of the modular mantle and configured to receive said detent.

15. The system of claim 13, wherein said means for securing said modular mantle to said first implant includes a means for preventing rotational movement of the first prosthetic implant within said modular mantle.

16. The system of claim 13, wherein said means for securing said first implant to said modular mantle includes a layer of bone cement, and wherein said modular mantle further includes at least one standoff body integral with, and extending from, said inner surface of said modular mantle.

17. The system of claim 8, further comprising a second prosthetic implant having an outer surface configured to complement said inner surface of said first implant and a means for securing said second prosthetic implant to said first implant.

18. The system of claim 17, wherein said first prosthetic implant is formed of a metallic material and said second prosthetic implant is formed of a polymeric material.

19. The system of claim 18, wherein said means for securing said second implant to said first implant includes a detent integral with, and extending from, the outer surface of the second implant, and a groove contained within the inner surface of the first implant and configured to receive said detent.

20. The system of claim 17, wherein said modular mantle is formed of a polymeric material.

21. The system of claim 20, further including a layer of bone cement applied between said outer surface of said first implant and said inner surface of said modular mantle, and wherein said mantle further includes at least one standoff body integral with, and extending from, said inner surface of said modular mantle.

22. The system of claim 21, further including a means for securing said mantle to said bone socket, wherein said securing means includes a layer of bone cement applied to said outer surface of said modular mantle.

23. The system of claim 17, wherein said modular mantle is formed of a bone growth inducing substance.

24. The system of claim 17, wherein said means for securing said second implant to said first implant includes a means for preventing rotational movement of said first prosthetic implant within said modular mantle.

25. The system of claim 8, wherein said modular mantle further includes at least one port through which a bone cement may be injected into the bone socket.

26. A modular cement mantle suitable for securing one or more prosthetic acetabular implants into an acetabulum, said modular mantle comprising an outer surface configured to complement an acetabulum and an inner surface configured to complement a prosthetic acetabular implant.

27. The modular cement mantle of claim 26, wherein said modular mantle further includes at least one port through which a bone cement may be injected into said acetabulum.

28. The modular cement mantle of claim 27, wherein said outer surface further includes at least two ribs integral with, and extending from, said outer surface.

29. The modular cement mantle of claim 26, wherein said inner surface further includes at least one standoff body integral with, and extending from, said inner surface.

30. The modular cement mantle of claim 21, further including a means for securing said modular mantle to said implant.

31. A modular prosthetic system for implantation into an acetabulum, said system comprising:

a prosthetic acetabular implant having an outer surface and an inner surface; and a modular mantle having an outer surface and an inner surface, wherein said inner surface of said modular mantle is configured to complement said outer surface of said implant, and said outer surface of said modular mantle is configured to complement an acetabulum.

32. The system of claim 31, wherein said modular mantle is formed of a polymeric material.

33. The system of claim 31, and further including a means for securing said implant to said modular mantle.

34. The system of claim 33, wherein said means for securing said modular mantle to said implant includes a detent integral with, and extending from, the outer surface of the implant, and a groove contained within the inner surface of the modular mantle and configured to receive said detent.

35. The system of claim 33, wherein said means for securing said modular mantle to said implant includes a means for preventing rotational movement of the implant within said modular mantle.

36. The system of claim 31, wherein said means for securing said implant to said modular mantle includes a layer of bone cement, and wherein said modular mantle further includes at least one standoff body integral with, and extending from, said inner surface of said modular mantle.

37. The system of claim 31, further including a means for securing said modular mantle to an acetabulum, said securing means including a layer of bone cement applied to said outer surface of said modular mantle and acetabulum.

38. The system of claim 37, wherein said means for securing said modular mantle to an acetabulum further includes a fastener engaged within each of at least one hole communicating through said modular mantle.

39. The system of claim 31, wherein said mantle includes at least one port through which a bone cement may be injected into the acetabulum.

* * * * *

UNITED STATES PATENT AND TRADEMARK OFFICE
CERTIFICATE OF CORRECTION

PATENT NO. : 5,658,338
DATED : August 19, 1997
INVENTOR(S) : Hugh S. Tullos and Philip C. Noble It is certified that error appears in the above-indentified patent and that said Letters Patent is hereby corrected as shown below:

At column 7, line 10, after "but" insert --not--.

In the claims:

In claim 30, line 1, change "21" to -- 26 --.

Signed and Sealed this

Seventh Day of April, 1998

Attest:

BRUCE LEHMAN

Attesting Officer      Commissioner of Patents and Trademarks